United States Patent [19]
Justice, Jr. et al.

[11] Patent Number: 4,588,484
[45] Date of Patent: May 13, 1986

[54] ELECTROCHEMICAL REDUCTION OF 3-CHLOROBENZO[B]THIOPHENES

[75] Inventors: Richard M. Justice, Jr.; David A. Hall, Indianapolis, both of Ind.

[73] Assignee: Eli Lilly and Company, Indianapolis, Ind.

[21] Appl. No.: 707,001

[22] Filed: Feb. 28, 1985

[51] Int. Cl.[4] .............................................. C25C 1/00
[52] U.S. Cl. ................................ 204/59 R; 204/73 R
[58] Field of Search ............................... 204/73, 59 R

[56] References Cited

U.S. PATENT DOCUMENTS 4,115,216 9/1978 Skaletz ............................. 204/73 R
4,402,803 9/1983 Hall .................................. 204/73 R

OTHER PUBLICATIONS

Renaud, "Electrochemical Synthesis . . . 1—Chloro-4-Methylnaphthalene", *Can. J. Chem.*, 52, 376, (1974).
Barba et al., "Cathodic Reduction . . . Mechanism" *Electrochimica Acta.*, vol. 27, No. 9, 1335, (1982).

Primary Examiner—John F. Niebling
Attorney, Agent, or Firm—Bruce J. Barclay; Arthur R. Whale

[57] ABSTRACT

The present invention relates to electrochemical reduction of a 3-chlorobenzo[b]thiophene to the corresponding 3-hydrobenzo[b]thiophene compound.

3 Claims, No Drawings

ELECTROCHEMICAL REDUCTION OF 3-CHLOROBENZO[B]THIOPHENES

SUMMARY OF THE INVENTION

The present invention relates to a process for preparing a 3-hydrobenzo[b]thiophene of the formula

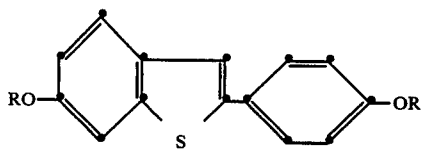

wherein each R independently is $C_1$–$C_4$ alkyl, $C_5$–$C_7$ cycloalkyl or benzyl, comprising electrochemically redpcing a 3-chlorobenzo[b]thiophene of the formula

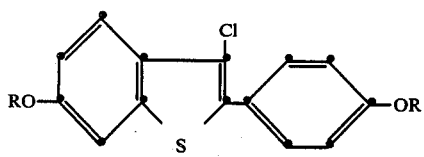

at or above the reduction potential required for the cleavage of the chlorine atom at the 3-position of a compound of formula II but below the reduction potential of a compound of formula I.

DETAILED DESCRIPTION OF THE INVENTION

The term "$C_1$–$C_4$ alkyl", as used herein, contemplates both straight and branched chain alkyl groups such as methyl, ethyl, n-propyl, isopropyl, n-butyl, t-butyl, isobutyl, and sec-butyl.

The term "$C_5$–$C_7$ cycloalkyl" represents cyclopentyl, cyclohexyl and cycloheptyl.

While the entire scope of process variables taught herein are believed operable, the present process does have preferred aspects. Both R groups preferably are $C_1$–$C_4$ alkyl, and especially methyl. Other preferred process conditions will be noted hereinafter.

The present process relates to the electrochemical reduction of a 3-chlorobenzo[b]thiophene according to the reaction conditions hereinafter specified to provide the corresponding 3-hydrobenzo[b]thiophene.

The process of the present invention is carried out with conventional electrolytic cells known in the electrochemical art. This invention does not provide and does not require the use of new cells or other equipment. Some discussion of electrolytic cells will be given, however.

A typical electrolytic cell of the type used for electrolytic reductions has a cathode at which reduction takes place. The cathode is maintained at a potential which is negative with respect to the anode at which only electrolyte reactions should take place. A reference electrode is usually used as well. The reference electrode, at which no reaction should take place, supplies a reference point from which the potential of the cathode is measured. Typical and frequently used reference electrodes are the saturated calomel electrode (S.C.E.) and the silver/silver chloride electrode. The reference electrode is electrically connected to the cathode through a conductive bridge or a porous junction.

The cells used in the instant invention are divided into compartments, so that each of the electrodes is immersed in fluid which is physically separated from the fluids of the other compartments, but is electrically connected to them.

The arrangement of electrolytic cells, the construction of electrodes, and the materials which may be effectively used as dividers are all part of the common knowledge of the electrochemical art, and are described in numerous textbooks and journal articles. Particularly useful textbooks which may be mentioned include *Organic Electrochemistry*, M. M. Baizer and H. Lund, Editors, Marcel Dekker, Inc., New York (1983), and *Technique of Electroorganic Synthesis*, N. L. Weinberg, Editor, John Wiley and Sons, New York, (1974).

Cathodes for use in this invention are made of glassy carbon, platinum, pyrolitic graphite, graphite, zinc, lead, or cadmium. The preferred cathodes are zinc and cadmium. The cathodes should be rather highly purified, as is typical in electrochemistry. The form of the electrode is not important; a solid sheet, gauze or cloth, a basket of shot, or a fluidized bed of particles, may all be used with equally good results. The cathode may also be made of an inert substrate plated with the cathode metal, or it may be made in the form of a sheet of the electrode composition, wrapped with gauze of the same composition to increase the electrode area.

The anode does not participate in the reductive process, and so it may be made of any suitable substance which is not attacked by the oxidative side of the electrolytic process. Anodes are usually made of the noble metals, especially platinum, or carbon. Platinum or the Dimentionally Stable Anode ® (ruthenium dioxide on titanium) of Diamond Shamrock Inc. are the preferred anodes.

It is most effective to arrange the cell so that the distance between the anode and the cathode is as small as possible. This relationship is desirable in all electrolytic processes in order to maximize current flow and minimize the temperature rise caused by the resistance of the fluid to the flow of the current.

The solvent used in the cathode compartment of the electrolytic cell employed in the process of the present invention can be a polar organic solvent. The polar organic solvent used in the present process should have a high dielectric constant and should not itself contain reducible groups such as a nitro group. Suitable polar organic solvents include dimethylformamide, acetonitrile, formamide, acetamide, N,N-dimethylacetamide, methanol, ethanol, isopropanol, tetrahydrofuran, acetone, N-methylformamide, and benzylnitrile. Preferred polar organic solvents are methanol, tetrahydrofuran, and acetonitrile.

Certain salts are used in the catholyte solution employed in the process of this invention. Suitable salts containing the ammonium cation for use in the catholyte include the simple ammonium salts such as ammonium chloride and ammonium acetate, and also more complex quaternary ammonium ions such as tetramethylammonium chloride, tetraethylammonium chloride, tetraethylammonium bromide, tetraethylammonium iodide, tetrapropylammonium iodide, tetrapropylammonium perchlorate, tetrabutylammonium perchlorate, tetrabutylammonium iodide, benzyltributylammonium chloride, benzyltriethylammonium chloride, methyltributylammonium iodide and tribenzylethylammonium p-toluenesulfonate.

The appropriate salt used in the catholyte solution is one that is soluble in the organic solvents described above. The concentration of the salt in the catholyte solvent is not critical; however, it is desirable to keep the concentration as high as possible to achieve the maximum conductivity of the resulting catholyte. Preferred salts for use in the catholytes of the process of this invention include tetraethylammonium perchlorate, tetramethylammonium chloride and especially tetraethylammonium chloride.

During the process of this invention the catholyte is preferably agitated by stirring, shaking or otherwise. It is desirable to provide sufficient agitation of the catholyte to keep the surface of the cathode thoroughly swept, so that a fresh supply of starting material is constantly supplied to the cathode.

The process of this invention is carried out in an electrolytic cell wherein the anode and cathode compartments are separated by a divider. The divider may be made from any of the materials commonly used in electrochemistry for this purpose. Particularly useful dividers are made from the ion exchange membranes, especially those which can pass cations. The divider used in the majority of the experimental examples of this invention is a perfluorosulfonic acid cation exchange resin sold by E. I. duPont de Nemours and Co., Wilmington, Del. under the tradename Nafion. Nafion 324 and 425 are preferred dividers. However, the dividers used in this invention are not limited to the above Nafion dividers. Dividers also may be advantageously made of finely porous substances such as ceramic membranes and sintered glass membranes. One such membrane is a microporous frit with a porosity of 0.9 to 1.4 microns. Such porous dividers may be made permeable to ions, but not to the fluids themselves, by sealing the membranes with a conductive gel, of which a typical example is agar gel saturated with an ionic substance such as, for example, potassium sulfate. Of course, the dividers used in the process of this invention should be compatible with the solvent used in the catholyte.

Since the anode occupies a cell compartment by itself, it is immersed in a conductive fluid. If the divider is a porous membrane, it is advisable to provide an anode fluid which is compatible with the catholyte. If the cell divider is porous only to ions, then the anolyte may be any convenient conductive fluid. A preferred anolyte is tetraethylammonium chloride dissolved in methanol.

The potential of the cathode, or the potential between the cathode and the anode, may be controlled in various ways. The most effective and precise way to control the potential is by use of a reference electrode, with its junction to the catholyte placed as physically close as possible to the cathode. The desired potential for the process is determined from an examination of a voltammogram of the system, and the potential between the cathode and the anode is adjusted to give the desired constant potential between the reference electrode and the cathode. This method of control is much more effective than control by the overall voltage between the cathode and the anode, since such voltage depends on the condition of the dividing membrane, as well as the concentration of the compound to be reduced in the catholyte.

It is relatively inefficient to control the reduction by means of a current flow between the anode and the cathode, because the current flow is directly dependent on the concentration of the compound to be reduced, as well as upon the physical condition of the electrodes and the divider. However, when an individual reduction has been thoroughly studied and the relationship between current, time and concentration is known, controlled current electrolysis can be used for the production of repeated batches.

Control of the reduction is best achieved by control of the potential between the reference electrode and the cathode or control of the current between the anode and the cathode. This control is best provided by an automatic instrument which constantly senses that potential or current and adjusts the voltage between the cathode and anode accordingly. Such instruments are available from commercial suppliers; for example, Princeton Applied Research, Inc., Princeton, N.J., USA supplies the PAR model 173 potentiostat/galvanostat.

The potential for operating the process of this invention with any given combination of electrodes, catholyte and compound is determined according to the routine method of the electrochemical art, i.e. by running a voltammogram of the system. In general, a voltammogram is run on the system first in the absence of substrate to determine the hydrogen production or background wave, followed by a voltammogram in the presence of substrate i.e. the 3-chloro-6-substituted-2-(4-substituted phenyl)benzo[b]thiophene. It has been found in performing voltammograms in the above manner under various conditions that the starting material reduction wave and the background wave are not sufficiently different in potential so as to operate at the current plateau in the starting material reduction wave without producing an undesirably large amount of hydrogen, i.e. an inefficient use of current. Indeed, it is frequently impossible to find a current plateau in the reduction wave of the starting material due to the plateau being obliterated by the background wave. Hence, it is necessary to examine the above initial voltammograms in order to select the potential where the fastest rate of reduction will occur while at the same time manifesting a highly efficient use of the current. In selecting this potential, it will be understood that some hydrogen production will most probably accompany the reduction, as we do not mean to imply that a desirable potential for the reduction is one where no hydrogen is produced.

It is not possible to specify a priori a precise potential range for the operation of the instant process with respect to a particular condition, since the potential for every system will necessarily vary. It has been observed, however, that the potential of the cathode for reductions according to this process is from about $-1.5$ volts to about $-2.5$ volts, relative to a saturated calomel reference electrode. The electrochemical reduction is conducted at or above the reduction potential required for the cleavage of the chlorine atom at the 3-position of a compound of formula II. The highest negative potential usable for this process would be at the degradation potential of a compound of formula I.

The reduction of this invention appears to be a 2-electron process, and so the reduction of a gram-mole of compound requires 192,974 coulombs. The length of time necessary to pass this amount of current necessarily depends upon the overall resistance of the cell, the effective area of the electrodes and the degree of agitation.

When the reduction is run in a constant potential fashion, typically the progress of the reaction is followed in at least one of the following ways. The number of amperes passed as a function of time is plotted, in order to approximately determine when the theoretically required number of coulombs has passed for completion of the reaction; or, more typically, the catholyte is periodically analyzed by high performance liquid chromatography to determine the amount of starting material and/or product that is present.

When the reduction process is conducted in a constant current fashion, the level of current used is chosen so as to give a fast reduction with high current efficiency. A preferred range for the constant current method is between about 2 to about 200 mA/cm$^2$.

The primary method for following the progress of a constant current reduction is analysis of the catholyte by high performance liquid chromatography. When constant current conditions are used, as the concentration of starting material decreases, the potential will increase. It therefore is necessary to monitor the potential over time and adjust it accordingly to prevent substantial amounts of hydrogen production. An additional way to predict the length of time the reduction should take at a constant current level is by simply figuring the amount of time necessary to pass the theoretically required amount of coulombs for the reduction of the desired benzothiophene.

The temperature at which the process is conducted is from above the freezing point of the liquid medium used to about 75° C., preferably from about 0° C. to about 30° C.

During the instant process it is desirable to purge oxygen from the cell by passing an inert gas such as nitrogen or argon through the catholyte. While not essential in the process, purging of oxygen enhances the efficiency of the reduction by preventing the consumption of coulombs by the reduction of any oxygen present.

The concentration of the benzothiophene in the catholyte is widely variable and is limited only by the solubility of the compound in the catholyte. It is most economical to use relatively high concentrations, in order to obtain the maximum effectiveness from the solvents used in the process.

The present process has been found to efficiently synthesize 3-hydrobenzo[b]thiophene derivatives in pure form. The present process is particularly advantageous in that the 3-chlorobenzo[b]thiophene starting material is often impure because of elemental sulfur. The presence of elemental sulfur adversely affects the yield of the reaction when employing most "wet" chemistry techniques. The purity of the starting material is irrelevant in the present process. Also the present process does not produce teratogens.

The compounds prepared by the present process are useful for a variety of purposes, but are preferably used as intermediates to compounds having antiestrogenic activity, that is, compounds having the ability to alleviate a pathological condition of an endocrine target organ. These compounds, including for instance [6-hydroxy-2-(4-hydroxyphenyl)benzo[b]thien-3-yl][4-[2-(1-piperidinyl)ethoxy]phenyl]methanone hydrochloride, and methods of their preparation from the compounds prepared by the present process, are taught in U.S. Pat. No. 4,418,068. The reader is also referred to U.S. Pat. No. 4,133,814 which teaches certain 2-phenyl-3-aroylbenzo[b]thiophenes useful as antifertility and anticancer agents.

The 3-chlorobenzo[b]thiophene derivatives used as starting materials for the present process are readily prepared by procedures well known to those skilled in the art, or by processes which are analogous to such prior art procedures. For example, one mole of a β-substituted styrene derivative may be reacted with a molar excess of thionyl chloride and from about 0.1 to 0.3 moles of pyridine at a temperature at or around the reflux temperature of the reaction mixture to afford the corresponding 3-chlorobenzo[b]thiophene. See *Synthesis* 670-3 (1981) and *J. Het. Chem.* 711-14 (1971).

The following Examples further illustrate specific aspects of the process of the present invention. The Examples are not intended to be limiting to the scope of the present process in any respect and should not be so construed.

Cell Description

The electrolysis cell employed in the following Examples consisted of two separate compartments. The cathode compartment was a 6 cm inside diameter jacketed beaker with an approximate volume of 160 ml.

The anode compartment was a 3.8 cm inside diameter polypropylene tube sized to fit inside the cathode compartment. The anode compartment was equipped with two collars. The first collar was friction fitted to the outside of the anode compartment and was used to adjust the depth of the anode compartment within the cathode compartment. The second collar and one end of the anode compartment were threaded such that a circular piece of cation exchange membrane could be used to seal off the tube forming a conductive water tight cup. The cation exchange membranes of choice were Nafion 425 and 324.

The cathode was a disk approximately 5.7 cm in diameter with a 0.7 cm wide, 9.5 cm long strip of insulated electrode material continuous with the disk and bent at right angles to it. The strip of electrode material was used for electrical contact.

The anode was a platinum wire ring sized to fit within the anode compartment with a straight piece of platinum wire continuous with the ring bent at right angles to it, used to make electrical contact.

A saturated calomel electrode with an appropriate electrolyte bridge was used as the reference for controlled potential experiments.

Controlled Potential Electrolysis

The cathode compartment was fitted with a cadmium cathode and a magnetic stirring bar. The cathode compartment was then charged with 30 ml of a 1.125 molar solution of tetraethylammonium chloride $((CH_3CH_2)_4N^+Cl^-)$ dissolved in 25 percent tetrahydrofuran/75 percent methanol (v/v). The solution was kept at a constant temperature of about 25° C. by means of a circulating refrigerated bath. One gram of 3-chloro-6-methoxy-2-(4-methoxyphenyl)benzo[b]thiophene was dissolved in the catholyte.

The anode compartment was fitted with a platinum wire anode, an anolyte presoaked Nafion 425 cation exchange membrane, and charged with 1.5 molar $(CH_3CH_2)_4N^+Cl^-$ dissolved in methanol. The anode compartment was then positioned within the cathode compartment. The anode compartment was charged with sufficient anolyte such that the level of the anolyte was approximately the same as the level of the catholyte. At this point, the catholyte was deoxygenated using a stream of inert gas and bubbler. The electrodes were then attached to the appropriate terminals of a potentiostat and a controlled potential of −2.0 V was applied for 1200 secs. The potential was then increased to −2.2 V. The reaction proceeded at this potential until complete as determined by HPLC monitor.

The product, 6-methoxy-2-(4-methoxyphenyl)benzo[b]thiophene, precipitated from solution. The electrolysis solution was transferred to a buchner funnel and filtered. The precipitated solid was washed with methanol and dried in a vacuum desiccator at 50° C. to provide 0.8068 g of 6-methoxy-2-(4-methoxyphenyl)benzo[b]thiophene. The product was produced at 85 percent current efficiency and recovered at 91 percent of theoretical yield.

| Elemental Analysis: | Analysis | Theory | Found |
|---|---|---|---|
| | C | 71.08 | 70.13 |
| | H | 5.22 | 4.63 |
| | O | 11.84 | 13.05 |
| | S | 11.86 | 11.72 |
| | Cl | 0 | 0.35 |
| | Residue | | 0.35 |

Mass spec. (electron impact): $M^+ = 270$.

NMR (270 MHz; CDCl$_3$): s, 3.85; s, 3.88; d, 6.94 (8.5); dd, 6.96 (8.5, 2.3); d, 7.29 (1.7); s, 7.33; d, 7.60 (8.5); d, 7.61 (8.5).

The following Examples illustrate controlled potential electrolysis conducted according to the general procedures outlined above.

The following key is meant to be referred to when determining the electrolyte employed in the Examples set forth in Table I. All percentages of solvent are determined by volume.

| Abbreviation | Electrolyte |
|---|---|
| A | 0.1M $(CH_3CH_2)_4N^+Cl^-$/methanol |
| B | 0.1M $(CH_3CH_2)_4N^+Cl^-$/acetonitrile |
| C | 1.5M $(CH_3CH_2)_4N^+Cl^-$/methanol |
| D | 0.75M $(CH_3CH_2)_4N^+Cl^-$/25% tetrahydrofuran/acetonitrile |
| E | 0.75M $(CH_3CH_2)_4N^+Cl^-$/35% tetrahydrofuran/acetonitrile |
| F | 1.5M $(CH_3CH_2)_4N^+Cl^-$/anhydrous methanol |
| G | 0.75M $(CH_3CH_2)_4N^+Cl^-$/25% tetrahydrofuran/anhydrous acetonitrile |
| H | 1.125M $(CH_3CH_2)_4N^+Cl^-$/25% tetrahydrofuran/anhydrous methanol |
| I | 0.75M $(CH_3CH_2)_4N^+Cl^-$/50% tetrahydrofuran/anhydrous methanol |
| J | 0.5M $(CH_3CH_2)_4N^+Cl^-$/anhydrous methanol |
| K | 0.5M $(CH_3CH_2)_4N^+Cl^-$/85% tetrahydrofuran/methanol |
| L | 0.5M $(CH_3CH_2)_4N^+Cl^-$/65% acetonitrile/tetrahydrofuran |
| M | 0.5M $(CH_3CH_2)_4N^+Cl^-$/85% tetrahydrofuran/anhydrous methanol |
| N | 0.45M $(CH_3CH_2)_4N^+Cl^-$/4% water/methanol |
| O | 0.45M $(CH_3CH_2)_4N^+Cl^-$/85% tetrahydrofuran/methanol |
| P | 1.0M $(CH_3CH_2)_4N^+Cl^-$/4% water/methanol |
| Q | 0.5M $(CH_3CH_2)_4N^+Cl^-$/75% tetrahydrofuran/methanol |
| R | 0.5M $(CH_3CH_2)_4N^+Cl^-$/65% tetrahydrofuran/methanol |

The following abbreviations were used to describe the anode and the cathode.
Zn=Zinc
Cd=Cadmium
Pt=Platinum

TABLE I

| | | | | | Controlled Potential Electrolysis | | | | |
|---|---|---|---|---|---|---|---|---|---|
| Example | Cathode | Catholyte | Anode | Anolyte | No. Coulombs | Potential vs. S.C.E. (v) | Quantity of Starting Material (g) | Quantity of Final Product (g) | Percent Yield |
| 2 | Zn | B | Pt | A | 1700 | −2.25 | 0.5013 | 0.2978 | 67 |
| 3 | Zn | D | Pt | C | 660 | −2.16 | 0.9998 | 0.6294 | 71 |
| 4 | Zn | D | Pt | C | 1551 | −2.20 | 1.0000 | 0.4345 | 49 |
| 5 | Zn | D | Pt | C | 1230 | −2.13 | 1.0013 | 0.4528 | 51 |
| 6 | Zn | D | Pt | C | 651 | −2.20 | 1.0027 | 0.2756 | 31 |
| 7 | Zn | E | Pt | C | 4891 | −2.20 | 2.1009 | 1.3785 | 74 |
| 8 | Zn | D | Pt | C | 2276 | −2.10 | 1.0004 | 0.3903 | 44 |
| 9 | Zn | D | Pt | C | 3884 | −2.20 | 0.9995 | 0.6292 | 71 |
| 10 | Zn | D | Pt | C | 2521 | −2.025 | 1.0000 | 0.5941 | 67 |
| 11 | Zn | D | Pt | C | 807 | −2.10 | 1.0012 | 0.4172 | 47 |
| 12 | Zn | D | Pt | C | 1489 | −2.16 | 0.9996 | 0.7091 | 80 |
| 13 | Zn | D | Pt | C | 698 | −2.10 | 1.0048 | 0.3297 | 37 |
| 14 | Zn | D | Pt | C | 704 | −2.15 | 1.0085 | 0.3845 | 43 |
| 15 | Zn | D | Pt | C | 1329 | −2.00 | 1.0010 | 0.6391 | 72 |
| 16 | Zn | D | Pt | C | 815 | −2.10 | 0.9997 | 0.4875 | 55 |
| 17 | Zn | G | Pt | F | 1483 | −2.10 | 1.0003 | 0.7184 | 81 |
| 18 | Cd | G | Pt | F | 2172 | −2.10 | 1.0001 | 0.7006 | 79 |
| 19 | Zn | G | Pt | F | 2094 | −2.10 | 1.0019 | 0.4886 | 55 |
| 20 | Zn | G | Pt | F | 850 | −2.10 | 1.0006 | 0.6477 | 73 |
| 21 | Cd | I | Pt | F | 852 | −2.00 | 1.8876 | 1.5231 | 91 |
| 22 | Cd | G | Pt | F | 2108 | −2.00 | 2.5013 | 2.0848 | 94 |
| 23 | Cd | G | Pt | F | 3232 | −2.00 | 2.5480 | 1.7397 | 77 |
| 24 | Cd | K | Pt | J | 3585 | −1.90 | 2.0011 | 1.5437 | 87 |
| 25 | Cd | K | Pt | J | 2137 | −2.00 | 2.0029 | 1.4918 | 84 |
| 26 | Cd | K | Pt | J | 2072 | −1.90 | 2.0200 | 1.6658 | 93 |
| 27 | Cd | L | Pt | J | 1006 | −2.25 | 2.0009 | 0.8161 | 46 |
| 28 | Zn | Q | Pt | P | 1917 | −2.20 | 2.5047 | 1.6435 | 74 |
| 29 | Zn | Q | Pt | P | 1594 | −2.30 | 2.5012 | 1.6412 | 74 |

Controlled Current Electrolysis

The cell description applies to a controlled current electrolysis as it does to a controlled potential electrolysis. However, controlled current experiments do not require the S.C.E. reference.

The cathode compartment was fitted with a cadmium cathode and a magnetic stirring bar. The cathode compartment was then charged with 40 ml of a 0.5 molar solution of $(CH_3CH_2)_4N^+Cl^-$ dissolved in 85 percent tetrahydrofuran/15 percent methanol (v/v). The solution was kept at a constant temperature of 25° C. by means of a circulating refrigerated bath. Two grams of 3-chloro-6-methoxy-2-(4-methoxyphenyl)benzo[b]thiophene were dissolved in the catholyte.

The anode compartment was fitted with a platinum wire anode and an anolyte presoaked Nafion 425 cation exchange membrane, and charged with 0.5 molar $(CH_3CH_2)_4N^+Cl^-$ dissolved in methanol. The anode compartment was then positioned within the cathode compartment. At this point, the catholyte was deoxygenated using a stream of inert gas. The electrodes were attached to the appropriate terminals of a d.c. power supply and a current of 15.7 mA cm$^{-2}$ was passed for 50 minutes, then a current of 9.8 mA cm$^{-2}$ was passed for 40 minutes until the completion of the reaction as determined by HPLC monitor (sample—10 microliters of concentration—0.8 mg/ml dissolved in 40:60 THF:eluent; eluent—80 percent $CH_3CN$/20 percent $H_2O$; program—iso; column—RCM C18; flow rate—3.0 ml min; pressure—1100 psi; Abs. range—1.0; UV filter—254 nm; cell path—10 mm).

The desired compound, 6-methoxy-2-(4-methoxyphenyl)benzo[b]thiophene, precipitated from solution. The solid was collected by vacuum filtration, washed with methanol and dried in a vacuum desiccator at 50° C. to provide 1.046 g of product. The product was produced at 59 percent current efficiency and recovered at 59 percent of theoretical yield. HPLC showed that the reaction was 84 percent completed when the electrolysis was stopped.

Additional Examples were conducted following the general controlled current electrolysis conditions outlined above. These results are set forth in Table II below.

TABLE II

Controlled Current Electrolysis

| Example | Cathode | Catholyte | Anode | Anolyte | No. Coulombs | Current Density (mAcm$^{-2}$) | Quantity of Starting Material (g) | Quantity of Final Product (g) | Percent Yield |
|---|---|---|---|---|---|---|---|---|---|
| 30 | Cd | K | Pt | J | 4000 | 16 | 2.0084 | 0.9973 | 56 |
| 31 | Cd | K | Pt | J | 3024 | 16 | 2.0009 | 1.2419 | 70 |
| 32 | Cd | K | Pt | J | 5520 | 16 | 2.0062 | 0.9784 | 55 |
| 33 | Cd | M | Pt | J | 2640 | 16–60 min 10–end | 2.0002 | 1.0996 | 62 |
| 34 | Cd | M | Pt | J | 2145 | 16–60 min 10–end | 2.0001 | 1.3301 | 75 |
| 35 | Cd | M | Pt | J | 2160 | 16–60 min 10–end | 2.0000 | 1.3478 | 76 |
| 36 | Cd | M | Pt | J | 2442 | 16–60 min 8–30 min 4–end | 1.9997 | 1.3298 | 75 |
| 37 | Cd | M | Pt | J | 1800 | 16–50 min 10–40 min | 2.0016 | 1.0471 | 59 |
| 38 | Zn | O | Pt | N | 4550 | 20 | 2.5026 | 1.2649 | 57 |
| 39 | Zn | K | Pt | P | 3432 | 16 | 2.48 | 0.3518 | 16 |
| 40 | Zn | Q | Pt | P | 2640 | 16 | 2.50 | 1.1305 | 51 |
| 41 | Zn | R | Pt | P | 2640 | 16 | 2.49 | 1.0598 | 48 |

We claim:

1. A process for preparing a 3-hydrobenzo[b]thiophene of the formula

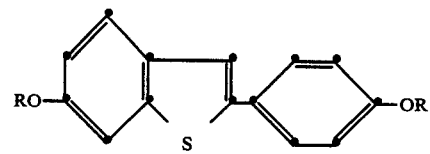

wherein each R independently is $C_1$–$C_4$ alkyl, $C_5$–$C_7$ cycloalkyl or benzyl, comprising electrochemically reducing a 3-chlorobenzo[b]thiophene of the formula

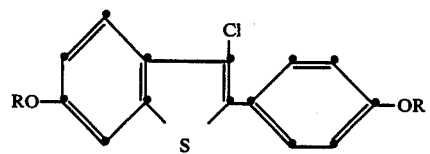

at or above the reduction potential required for the cleavage of the chlorine atom at the 3-position of a compound of formula II but below the reduction potential of a compound of formula I.

2. A process of claim 1 wherein each R independently is $C_1$–$C_4$ alkyl.

3. A process of claim 2 wherein each R is methyl.

* * * * *